United States Patent [19]

Schonafinger et al.

[11] Patent Number: 4,743,601
[45] Date of Patent: May 10, 1988

[54] DIHYDRO-1,4-OXAZINO(2,3-C)QUINO-LINES

[75] Inventors: Karl Schonafinger, Alzenau, Fed. Rep. of Germany; Helen H. Ong, Whippany, N.J.

[73] Assignee: Hoechst-Roussel Pharmaceuticals Inc., Somerville, N.J.

[21] Appl. No.: 72,832

[22] Filed: Jul. 13, 1987

[51] Int. Cl.$^4$ .................. A61K 31/535; A61K 31/54; C07D 498/04; C07D 513/20
[52] U.S. Cl. ..................... 514/229.8; 544/6; 544/62; 544/71; 544/101; 544/128; 546/159; 546/163; 514/228.5
[58] Field of Search .................. 544/101, 6, 71; 514/222, 227, 236, 237, 239

[56] References Cited

U.S. PATENT DOCUMENTS 4,420,480 12/1983 Jones .................. 544/101 X

Primary Examiner—Richard L. Raymond
Attorney, Agent, or Firm—Tatsuya Ikeda

[57] ABSTRACT

There are disclosed novel compounds of the formula

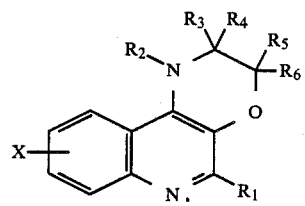

where X is hydrogen, loweralkyl, loweralkoxy, hydroxy, halogen, nitro or trifluoromethyl; $R_1$ is hydrogen or loweralkyl; $R_2$ is hydrogen, loweralkyl, arylloweralkyl or —$(CH_2)_mR_7$ wherein m is 1, 2 or 3 and $R_7$ is cyano or amino; $R_3$ and $R_4$ are independently hydrogen or loweralkyl; $R_5$ and $R_6$ are independently hydrogen or loweralkyl, or $R_5+R_6$ taken together with the carbon atom to which they are attached constitute a cyclobutane, cyclopentane, cyclohexane, cycloheptane, pyrrolidine, piperidine, morpholine or thiomorpholine ring, or $R_5$ is hydrogen and $R_6$ is aryl or —$CH_2OR_8$ wherein $R_8$ is hydrogen, loweralkyl or loweralkylcarbonyl, which are useful for enhancing memory.

25 Claims, No Drawings

DIHYDRO-1,4-OXAZINO(2,3-C)QUINOLINES

The present invention relates to novel compounds of the formula,

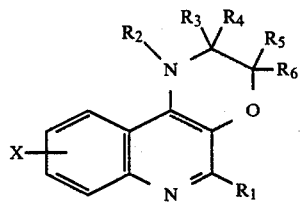

where X is hydrogen, loweralkyl, loweralkoxy, hydroxy, halogen, nitro or trifluoromethyl; $R_1$ is hydrogen or loweralkyl; $R_2$ is hydrogen, loweralkyl, arylloweralkyl or $-(CH_2)_mR_7$ wherein m is 1, 2 or 3 and $R_7$ is cyano or amino; $R_3$ and $R_4$ are independently hydrogen or loweralkyl; $R_5$ and $R_6$ are independently hydrogen or loweralkyl, or $R_5+R_6$ taken together with the carbon atom to which they are attached constitute a cyclobutane, cyclopentane, cyclohexane, cycloheptane, pyrrolidine, piperidine, morpholine or thiomorpholine ring, or $R_5$ is hydrogen and $R_6$ is aryl or $-CH_2OR_8$ wherein $R_8$ is hydrogen, loweralkyl or loweralkylcarbonyl, which are useful for enhancing memory; to pharmaceutical compositions comprising an effective memory enhancing amount of such a compound; and to a method of treating a patient in need of memory enhancement which comprises administration of an effective amount of such a compound.

This invention also relates to novel compounds of the formula,

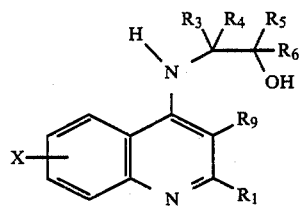

where X, $R_1$ and $R_3$ through $R_6$ are as defined earlier and $R_9$ is hydrogen or bromine (with the proviso that when $R_1=R_3=R_4=R_5=R_6=R_9=H$, X is not 7-chloro) which are also useful for enhancing memory and for preparing compounds of formula I.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl group include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unelss otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen or $CF_3$, and the term diaryl shall mean two such aryl groups each of which being independent of the other.

The compounds of this invention are prepared by following one or more of the steps described below. Throughout the description of the synthetic steps, the definitions of X and $R_1$ through $R_9$ are as given above unless otherwise stated or indicated.

STEP A

A compound of formula III is reacted with a primary amine of formula IV to afford a compound of formula V.

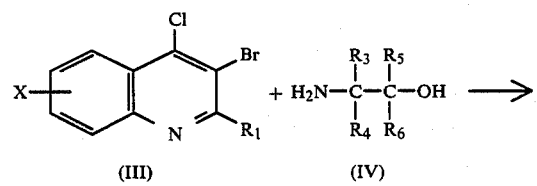

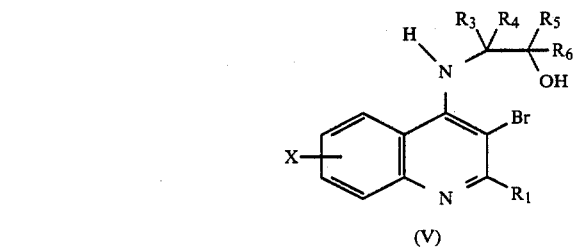

This reaction is typically conducted in a suitable solvent, for instance, a polar solvent such as butanol, 2-ethoxyethanol or the like and by stirring the reaction mixture at a temperature of about 100°–180° C. Reflux condition is preferred. Optionally, triethylamine may be added to the reaction mixture in order to facilitate the reaction. Presence of solvent is not essential.

Alternatively to the above, the following two steps may be used to obtain compound V.

STEP B

A compound of formula VI is reacted with compound IV in substantially the same manner as in STEP A to afford a compound of formula VII.

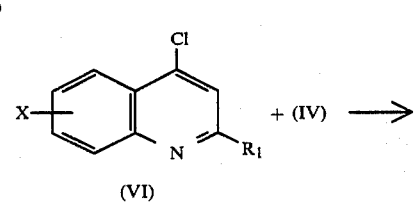

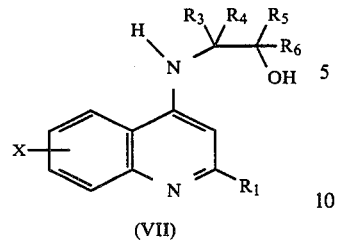

(VII)

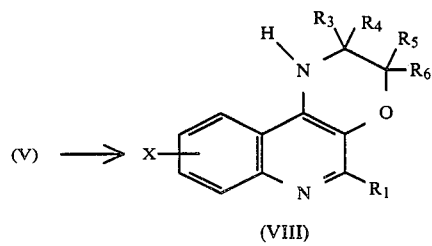

(VIII)

STEP C

Compound VII is reacted with bromine to afford compound V.

(VII)+BR$_2$→(V)

This reaction is typically conducted at room temperature in the presence of a suitable solvent such as acetic acid.

STEP D

Sometimes, it is convenient to obtain a compound of formula Va from the corresponding chloro compound of formula Vb by use of hydrogenolysis.

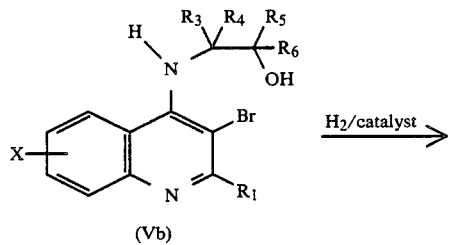

(Vb)

 H$_2$/catalyst

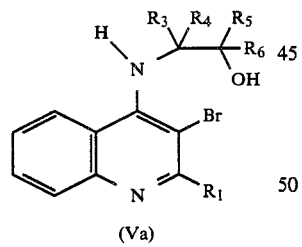

(Va)

This hydrogenolysis is typically conducted in the presence of a suitable noble metal catalyst suchas palladium on carbon and a suitable reaction medium such as methanol. It is preferable to add small amounts of acetic acid and sodium acetate to the reaction system. The reaction is typically conducted at room temperature while the mixture is being shaken.

STEP E

Compound V obtained from one of the foregoing steps is cyclized to afford a compound of formula VIII.

This cyclization is typically conducted in the presence of a suitable solvent such as dimethylformamide and a strong base such as potassium tertiary butoxide or sodium hydride and by stirring the reaction mixture at a temperature of about 70°–150° C.

STEP F

Compound VIII is reacted with a loweralkyl chloride or arylloweralkyl chloride of the formula R$_{10}$—Cl where R$_{10}$ is loweralkyl or arylloweralkyl in a routine manner known to the art to obtain a compound of formula IX.

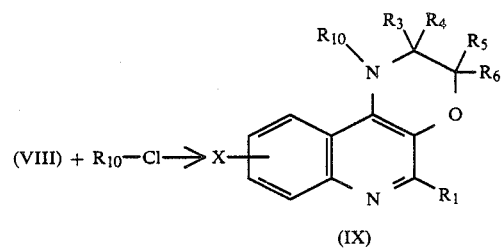

(IX)

STEP G

Compound VIII is reacted with a compound of formula X in a routine manner known to the art to obtain a compound of formula XI.

(VIII) + NC—(CH$_2$)$_m$—Br ⟶

(X)

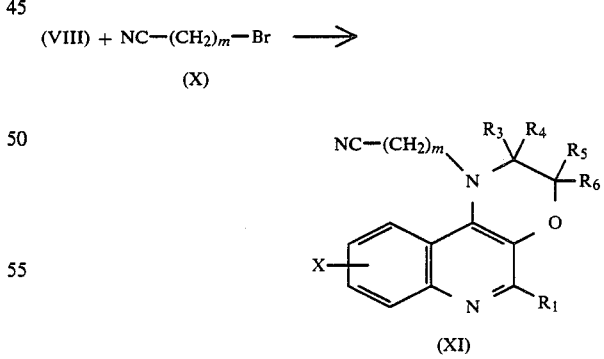

(XI)

Alternatively to the above, where m is 2 in formula XI, the desired product can also be obtained by reacting compound VIII with acrylonitrile rather than NCCH$_2$CH$_2$Br in a routine manner known to the art.

STEP H

Compound XII is reduced in a routine manner known to the art to obtain a compound of formula XII.

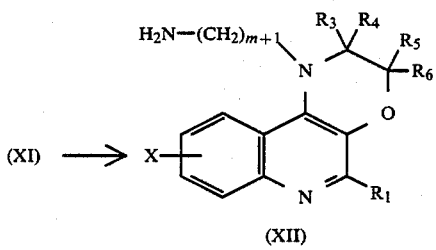

The compounds of formula I and II of the present invention are useful in the treatment of various memory dysfunctions characterized by decreased cholinergic function, such as Alzheimer's disease.

This utility is demonstrated by the ability of these compounds to restore cholinergically deficient memory in the Dark Avoidance Assay, where they are in general active over a broader dose range than heretofore known compounds, a distinct therapeutic advantage.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic agent that is known to cause memory impairment, is administered before an animals' initial exposure to the test chamber, the animal re-enters the dark compartment shortly after being placed in the test chamber 24 hours later. This effect of scopolamine is blocked by an active test compound, resulting in greater interval before re-entry into the dark compartment.

The results for an active compound are expressed as the percent of a group of animals in which the effect of scopolamine is blocked, as manifested by an increased interval between being placed in the test chamber and re-entering the dark compartment. Results for some of the compounds of this invention are presented in Table 1.

TABLE 1

| Compound | Dose (mg/kg of Body Weight), s.c. | % of Animals With Scopolamine Induced Memory Deficit Reversed |
| --- | --- | --- |
| 1,2-dihydro-3-methyl-3H—1,4-oxazino[2,3-c]quinoline | 0.16<br>2.50 | 27%<br>47% |
| 7-chloro-N—(2-hydroxypropyl-4-quinolinamine | 1.25<br>2.50 | 27%<br>47% |
| 8-chloro-1,2-dihydro-2-methyl-3H—1,4-oxazino-[2,3-c]quinoline | 0.16 | 21% |
| 3-bromo-N—(2,3-dihydroxypropyl)-2-methyl-4-quinolinamine (reference compound) | 0.31 | 40% |
| Physostigmine | 0.31 | 20% |

Effective quantities of the compounds of the invention may be administered to a patient by any of the various methods, for example, orally as in capsules or tablets, parenterally in the form of sterile solutions or suspensions, and in some case intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, malic, fumaric and oxalic acids.

The active compounds of the present invention may be orally administered, for example, with an inert diluent or with an edible carrier, or they may be enclosed in gelatin capsules, or they may be compressed into tablets. For the purposes of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit form may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as as ethylenediaminetetraacetic acid; buffers such as acetates, citrates or phosphate and agents for the adjustment of tonicity such as sodium chloride or dextrose. The parenteral preparation can be enclosed in disposable syringes or multiple dose vials made of glass or plastic.

Examples of compounds according to this invention include:

N-(2-hydroxyethyl)-4-quinolinamine;
7-chloro-N-(2-hydroxy-1-methylethyl)-4-quinolinamine;
7-chloro-N-(2-hydroxy-1-phenylethyl)-4-quinolinamine;
7-chloro-N-(2-hydroxypropyl)-4-quinolinamine;
N-(2,3-dihydroxypropyl)-2-methyl-4-quinolinamine;
7-chloro-N-(2-hydroxy-2-phenylethyl)-4-quinolinamine;
N-(2-hydroxy-2-phenylethyl)-4-quinolinamine;
7-chloro-N-[(1-hydroxycyclohexyl)methyl]-4-quinolinamine;
3-bromo-N-(2-hydroxyethyl)-4-quinolinamine;
3-bromo-N-(2-hydroxyethyl)-2-methyl-4-quinolinamine;
3-bromo-7-chloro-N-(2-hydroxyethyl)-4-quinolinamine;
3-bromo-N-(2-hydroxyethyl)-7-trifluoromethyl-4-quinolinamine;
3-bromo-7-chloro-N-(2-hydroxy-1-methylethyl)-4-quinolinamine;
3-bromo-N-(2-hydroxypropyl)-4-quinolinamine;
3-bromo-N-(2-hydroxypropyl)-2-methyl-4-quinolinamine;
3-bromo-7-chloro-N-(2-hydroxypropyl)-4-quinolinamine;
3-bromo-N-(2,3-dihydroxypropyl)-2-methyl-4-quinolinamine;
3-bromo-N-(2-hydroxy-2-phenylethyl)-4-quinolinamine;
3-bromo-N-(1-hydroxycyclohexylmethyl)-4-quinolinamine;
3-bromo-7-chloro-N-(1-hydroxycyclohexylmethyl)-4-quinolinamine;
1,2-dihydro-3H-1,4-oxazino[2,3-c]quinoline;
1,2-dihydro-5-methyl-3H-1,4-oxazino[2,3-c]quinoline;
8-chloro-1,2-dihydro-3H-1,4-oxazino[2,3-c]quinoline;
8-chloro-1,2-dihydro-2-methyl-3H-1,4-oxazino[2,3-c]quinoline;
1,2-dihydro-3-methyl-3H-1,4-oxazino[2,3-c]quinoline;
1,2-dihydro-3,5-dimethyl-3H-1,4-oxazino[2,3-c]quinoline;
8-chloro-1,2-dihydro-3-methyl-3H-1,4-oxazino[2,3-c]quinoline;
1,2-dihydro-3-hydroxymethyl-3H-5-methyl-1,4-oxazino[2,3-c]quinoline;
1,2-dihydro-3-phenyl-3H-1,4-oxazino[2,3-d]quinoline;
spiro[cyclohexane-1,3'-[3H][1,4]oxazino[2,3-c]quinoline];
8'-chloro-spiro[cyclohexane-1,3'-[3H][1,4]oxazino[2,3-c]quinoline; and
1-(2-cyanoethyl)-1,2-dihydro-3H-1,4-oxazino[2,3-c]quinoline;

The following examples are presented in order to illustrate this invention.

EXAMPLE 1

N-(2-hydroxyethyl)-4-quinolinamine

A slurry of 0.86 g of palladium on carbon in isopropanol was pipetted into a Parr shaker and to this was added a solution of 10 of 7-chloro-N-(2-hydroxyethyl)-4-quinolinamine and 6.1 g of sodium acetate in 260 ml of methanol and 7 ml of acetic acid. The mixture was hydrogenated at 51 psi (pounds per square inch) until no further reaction was observed. Upon filtration through celite and evaporation of solvents an oil resulted which was dissolved in water and basified with sodium hydroxide. A solid resulted which was recrystallized from isopropanol to give 8.5 g of purifed compound with a melting point of 152°–154° C.

Analysis: Calculated for $C_{11}H_{12}N_2O$: 70.19%C; 6.43%H; 14.89%N. Found: 69.63%C; 6.48%H; 14.66%N.

EXAMPLE 2

7-Chloro-N-(2-hydroxy-1-methylethyl)-4-quinolinamine

A mixture of 20 g of 4,7-dichloroquinoline and 16 g of 2-amino-1-propanol in 60 ml of butanol was stirred at reflux. The reaction was complete after three days of stirring and the vessel was allowed to cool to room temperature. Water was added to the mixture and extraction was conducted with dichloromethane. Drying over anhydrous magnesium sulfate and evaportion of solvents resulted in 17 g of solid which was triturated with ether. Recrystallization from ethanol/acetone gave 16 g of crystalline solid with a melting point of 210°–212° C.

Analysis: Calculated for $C_{12}H_{13}ClN_2O$: 60.89%C; 5.53%H; 11.84%N. Found: 60.72%C; 5.71%H; 11.72%N.

EXAMPLE 3

7-Chloro-N-(2-hydroxy-1-phenylethyl)-4-quinolinamine

A mixture of 20 g of 4,7-dichloroquinoline and 14 g of D-(−)-phenylglycinol in 60 ml of butanol and 17 ml of triethylamine was stirred at reflux. The reaction was complete after two days of stirring and the vessel was allowed to cool to room temperature. The mixture was diluted with 75 ml of water and extracted with dichloromethane (3×100 ml). Drying over anhydrous magnesium sulfate and evaporation of solvents resulted in an oil which crystallized upon standing. The solid was purified by HPLC using 16:1 dichloromethane/methanol as the eluent. Recrystallization from ethanol/acetone gave 18 g of solid with a melting point of 220°–221° C.

Analysis: Calculated for $C_{17}H_{15}ClN_2O$: 68.34% C; 5.06%H; 9.38%N. Found: 68.44%C; 5.20%H; 9.29%N.

EXAMPLE 4

7-Chloro-N-(2-hydroxypropyl)-4-quinolinamine

A mixture of 20 g of 4,7-dichloroquinoline and 16 g of 1-amino-2-propanol in 60 ml of butanol was stirred at reflux until the reaction was complete (6 hours). The reaction mixture was cooled down to room temperature and diluted with water. The organics were exracted into dichloromethane (3×300 ml). Drying over anhydrous magnesium sulfate and evaporation of solvents resulted in an oil which crystallized upon standing. The crystals were isolated by filtration and washed with ether to yield a solid which was recrystallized from isopropanol. The resultant crystals had a melting point of 168°–169.5° C. and the yield was 15 g.

Analysis: Calculated for $C_{12}H_{13}ClN_2O$: 60.89%C; 5.53%H; 11.84%N.
Found: 60.66%C; 5.39%H; 11.73%N.

EXAMPLE 5

N-(2,3-dihydroxypropyl)-2-methyl-4-quinolinamine

A mixture of 4-chloro-2-methylquinoline (50 g) and 3-amino-1,2-propandiol (51 g) was heated at 160° C. for 1 hour. The mixture while still hot was poured into 700 ml of water. The mixture was saturated with potassium carbonate and cooled in an ice bath, whereupon the product crystallized. It was filtered and recrystallized from ethanol. The yield was 55 g, mp 167°–168° C.

Analysis: Calculated for $C_{13}H_{16}N_2O_2$: 67.22%C; 6.94%H; 12.06%N. Found: 67.08%C; 7.16%H; 12.07%N.

EXAMPLE 6

7-Chloro-N-(2-hydroxy-2-phenylethyl)-4-quinolinamine

A solution of 4,7-dichloroquinoline (19.8 g), 2-amino-1-phenylethanol (13.7 g) and 20 ml of triethylamine (14.5 g) in 10 ml of ethoxyethanol was heated at 130° C. overnight. The mixture was poured into 600 ml of water and the solid product was collected by filtration, recrystallized from ethoxyethanol and washed with ethanol. The yield was 16 g, mp 221°–222° C.

Analysis: Calculated for $C_{17}H_{15}ClN_2O$: 68.34%C; 5.03%H; 9.38%N. Found: 68.33%C; 4.98%H; 9.40%N.

EXAMPLE 7

N-(2-hydroxy-2-phenylethyl)-4-quinolinamine

A mixture of 7-chloro-N-(2-hydroxy-2-phenylethyl)-4-quinolinamine (10 g), 0.8 g of palladium on powdered charcoal (10%), 5 ml of acetic acid, 7 g of sodium acetate.3H$_2$O and 200 ml of methanol was hydrogenated at room temperature with shaking at 30–50 psi until completion of hydrogen uptake. The catalyst was filtered and the solvent evaporated. The oil residue was dissolved in 20 ml of water and the solution made alkaline (pH=10) with and NaOH solution. The crystalline compound was filtered and recrystallized from isopropanol. The yield was 7.5 g, mp 289°–290° C.

Analysis: Calculated for $C_{17}H_{16}N_2O$: 77.27%C; 6.06%H; 10.61%N. Found: 77.03%C; 6.05%H; 10.59%N.

EXAMPLE 8

7-Chloro-N-[(1-hydroxycyclohexyl)methyl]-4-quinolinamine

A solution of 20 g of 4,7-dichloroquinoline, 20 g of 1-aminomethyl-1-cyclohexanol hydrochloride and 3 equivalents of triethylamine in 80 ml of 2-ethoxyethanol was stirred at reflux until the reaction was complete. The reaction was complete after 16 hours, and upon dilution of the reaction mixture with water (300 ml), a solid precipitated out which was isolated by filtration. Recrystallization from ethanol gave 16 g of crystalline solid with a melting point of 205°–207° C.

Analysis: Calculated for $C_{16}H_{19}ClN_2O$: 66.08%C; 6.59%H; 9.64%N. Found: 66.35%C; 6.61%H; 9.75%N.

EXAMPLE 9

3-Bromo-N-(2-hydroxyethyl)-4-quinolinamine

A mixture of 9.1 g of 3-bromo-4-chloro-quinoline and 2.0 g of ethanolamine was heated at 150° C. for 30 minutes. The reaction mixture was cooled, 60 ml of water was added and the precipitate was collected by filtration and recrystallized from isopropanol. The yield was 9.5 g, mp 163°–165° C.

Analysis: Calculated for $C_{11}H_{11}BrN_2O$: 49.44%C; 4.12%H; 10.49%N. Found: 49.31%C; 4.19%H; 10.32%N.

EXAMPLE 10

3-Bromo-N-(2-hydroxyethyl)-2-methyl-4-quinolinamine

Bromine (15.6 g) was added dropwise to a solution of N-(2-hydroxyetyl)-2-methyl-4-quinolinamine (26 g) in 400 ml of acetic acid. A solid separated which after one hour of stirring was filtered and dissolved in 400 ml of water. The free base was precipitated by adding 20% KOH solution until pH became 10. The solid was filtered and recrystallized from isopropanol. The yield was 14.5 g, mp 154°–155° C.

Analysis: Calculated for $C_{12}H_{13}BrN_2O$: 51.26%C; 4.66%H; 9.97%N. Found: 51.17%C; 4.75%H; 10.04%N.

EXAMPLE 11

3-Bromo-7-chloro-N-(2-hydroxyethyl)-4-quinolinamine

Bromine (4.3 g) was added dropwise to a solution of 7-chloro-N-(2-hydroxyethyl)-4-quinolinamine (6 g) in 60 ml of acetic acid. The mixture was stirred overnight and the solid separated by filtration. This solid was dispensed in 100 ml of water and the mixture made alkaline (pH=8) with a sodium bicarbonate solution. After two hours of stirring, the product was filtered and recrystallized twice from isopropanol and from ethanol. The yield was 3.5 g, mp 169°–170° C.

Analysis: Calculated for $C_{11}H_{10}BrClN_2O$: 43.78%C; 3.32%H; 9.29%N. Found: 43.44%C; 3.24%H; 9.10%N.

EXAMPLE 12

3-Bromo-N-(2-hydroxyethyl)-7-trifluoromethyl-4-quinolinamine

A solution of 12.4 g of 3-bromo-4-chloro-7-trifluoromethylquinoline and 6.1 g of 2-aminoethanol in 30 ml of isopropanol was heated at reflux for 4 hours. The mixture was cooled and diluted with 150 ml of water and the solid was collected and recrystallized from isopropanol. The yield was 8.2 g, mp 140°–141° C.

Analysis: Calculated for $C_{12}H_{10}BrF_3N_2O$: 43.00%C; 2.99%H; 8.36%N. Found: 42.94%C; 3.07%H; 8.32%N.

EXAMPLE 13

3-Bromo-7-chloro-N-(2-hydroxy-1-methylethyl)-4-quinolinamine

A mixture of 12 g of 7-chloro-N-(2-hydroxy-1-methylethyl)-4-quinolinamine and 112 ml of acetic acid was stirred at room temperature and to it 8 g of bromine was added dropwise over a thirty minute period. The product precipitated from the solution as the hydrobromide salt and it was isolated by filtration, dissolved in water and basified with sodium hydroxide. The free base was extracted into dichloromethane and evaporation of solvents resulted in a solid which was purified by HPLC using 95:5 dichloromethane/methanol as the eluent. Recrystallization from isopropanol yielded 9 g of crystalline solid with a melting point of 145°–147° C.

Analysis: Calculated for $C_{12}H_{12}BrClN_2O$: 45.67%C; 3.83%H; 8.88%N. Found: 45.77%C; 3.82%H; 8.81%N.

EXAMPLE 14

3-Bromo-N-(2-hydroxypropyl)-4-quinolinamine

A mixture of 3 g of 3-bromo-4-chloro-quinoline and 10 g of aminopropanol-2 was heated to 150° C. for 20 minutes. The mixture was cooled and poured into 120 ml of water and the product was extracted with 100 ml of ether. The ether layer was dried over sodium sulfate, the solvent removed by evaporation and the residue recrystallized from ether/hexane. The yield was 2.6 g, mp 82°-83° C.

Analysis: Calculated for $C_{12}H_{13}BrN_2O$: 51.25%C; 4.63%H; 9.96%N. Found: 50.85%C; 4.51%H; 9.80%N.

EXAMPLE 15

3-Bromo-N-(2-hydroxypropyl)-2-methyl-4-quinolinamine

Bromine (32 g) was added dropwise to a solution of 44 g of N-(2-hydroxypropyl)-2-methyl-4-quinolinamine in 600 ml of acetic acid. The solution was stirred for 1 hour and the HBr salt was filtered and washed with a small amount of acetic acid. It was then dissolved in 500 ml of water and an aqueous KOH solution was added, whereupon the free base precipitated. It was filtered and recrystallized from isopropanol. The yield was 22 g, mp 147°-149° C.

Analysis: Calculated for $C_{13}H_{15}BrN_2O$: 52.89%C; 5.12%H; 9.49%N. Found: 52.74%C; 5.14%H; 9.35%N.

EXAMPLE 16

3-Bromo-7-chloro-N-(2-hydroxypropyl)-4-quinolinamine

A mixture of 12 g of 7-chloro-N-(2-hydroxypropyl)-4-quinolinamine in 112 ml of acetic acid was stirred at room temperature and to it 8 g of bromine was added dropwise over a thirty minute period. After 1.5 hours, a solid formed which was isolated by filtration, dissolved in water and basified with sodium hydroxide, whereupon a solid formed which was collected by filtration. Recrystallization from ethanol yielded 8 g of solid with a melting point of 161°-163° C.

Analysis: Calculated for $C_{12}H_{12}BrClN_2O$: 45.67%C; 3.83%H; 8.88%N. Found: 45.27%C; 3.74%H; 8.76%N.

EXAMPLE 17

3-Bromo-N-(2,3-dihydroxypropyl)-2-methyl-4-quinolinamine

Bromine (33.7 g) was added dropwise to a solution of 49 g of N-(2,3-dihydroxypropyl)-2-methyl-4-quinolinamine in 600 ml of acetic acid. After two hours of stirring, the resultant oil was separated by decantation, dissolved in 500 ml of water and the mixture made alkaline (pH=10) with potassium carbonate. The resultant free base solid was filtered and recrystallized from ethanol. The yield was 33 g, mp 140°-141° C.

Analysis: Calculated for $C_{13}H_{15}BrN_2O_2$: 50.17%C; 4.86%H; 9.00%N. Found: 49.86%C; 4.91%H; 8.85%N.

EXAMPLE 18

3-Bromo-N-(2-hydroxy-2-phenylethyl)-4-quinolinamine

A solution of 4 g of 3-bromo-4-chloro-quinoline and 6 g of 2-hydroxy-2-phenyl-ethylamine was heated at 150° C. for 3 hours in 10 ml of ethoxyethanol. The mixture was cooled and poured into 150 ml of water. The product was extracted with two 50 ml portions of ether. The ether layer was dried over sodium sulfate, the solvent was evaporated and the residue was recrystallized from isopropanol. The yield was 3.0 g, mp 131°-132° C.

Analysis: Calculated for $C_{17}H_{15}BrN_2O$: 59.48%C; 4.37%H; 8.16%N. Found: 59.04%C; 4.34%H; 8.01%N.

EXAMPLE 19

3-Bromo-N-(1-hydroxycyclohexylmethyl)-4-quinolinamine

A mixture of 3-bromo-4-chloroquinoline (12.1 g), 1-aminomethyl-1-cyclohexanol.HCl (8.3 g), triethylamine (7.2 g) and 30 ml of ethoxyethanol was stirred at 120° C. for 5 hours and poured into 250 ml of ice water. The solid was filtered and recrystallized from acetone. The yield was 6.5 g, mp 130°-132° C.

Analysis: Calculated for $C_{16}H_{19}BrN_2O$: 57.33%C; 5.67%H; 8.36%N. Found: 56.97%C; 5.67%H; 8.17%N.

EXAMPLE 20

3-Bromo-7-chloro-N-(1-hydroxycyclohexylmethyl)-4-quinolinamine

A solution of 11.2 g of 7-chloro-N-(1-hydroxycyclohexylmethyl)-4-quinolinamine in 130 ml of glacial acetic acid was stirred at room temperature and 6.15 g of bromine was added dropwise. The product precipitated from the solution as the hydrobromide salt and was isolated by filtration. The solid was then suspended in water and basified with sodium hydroxide. After two hours of stirring, the solid was collected by filtration. By combustion analysis, the product proved to be a hemi-hydrobromide salt, and therefore, it was necessary to dissolve the solid in methanol and 1 equivalent of trietylamine with heating. A solid resulted which was recrystallized from ethanol to give 7 g of crystalline solid with a melting point of 151°-154° C.

Analysis: Calculated for $C_{16}H_{18}BrClN_2O$: 51.98%C; 4.91%H; 7.56%N. Found: 51.70%C; 4.98%H; 7.36%N.

EXAMPLE 21

1,2-Dihydro-3H-1,4-oxazino[2,3-c]quinoline

A mixture of 8.0 g of 3-bromo-N-(2-hydroxyethyl)-4-quinolinamine and 4 g of potassium-tert-butoxide in 220 ml of dimethylformamide was heated at reflux for 3 hours. The reaction mixture was cooled to room temperature and diluted with 200 ml of water and the product was extracted with 4 portions of 50 ml of dichloromethane (DCM). The DCM solution was dried over sodium sulfate and concentrated. The oily residue was dissolved in 150 ml of ethanol. To this solution 5 ml of concentrated HCl was added, the HCl salt was separated by filtration and recrystallized from ethanol. This crystalline material was dissolved in 75 ml of water and the solution made alkaline (pH=8) with a sodium bicarbonate solution. The free base was filtered and dried in vacuo to yield 1.3 g of white solid, mp 175°-176° C.

Analysis: Calculated for $C_{11}H_{10}N_2O$: 70.97%C; 5.38%H; 15.05%N. Found: 70.40%C; 5.21%H; 14.84%N.

EXAMPLE 22

1,2-Dihydro-5-methyl-3H-1,4-oxazino[2,3-c]quinoline

A mixture of 3-bromo-N-(2-hydroxyethyl)-2-methyl-4-quinolinamine (11.5 g), potassium-tert-butoxide (3.7 g) and 100 ml of dimethylformamide (DMF) was stirred at 80° C. for 3 hours. The mixture was cooled and diluted with 600 ml of water and thereafter kept in a refrigerator for 2 days. The resultant solid was filtered and recrystallized from isopropanol. The yield was 3.3 g, mp 203°–204° C.

Analysis: Calculated for $C_{12}H_{12}N_2O$: 71.97%C; 6.04%H; 13.99%N. Found: 71.49%C; 6.20%H; 13.78%N.

EXAMPLE 23

8-Chloro-1,2-dihydro-3H-1,4-oxazino[2,3-c]quinoline

Sodium hydride (obtained from 3 g of 50% suspension in mineral oil) was added to a solution of 3-bromo-7-chloro-N-(2-hydroxyethyl)-4-quinolinamine (15 g) in 30 ml of DMF and the mixture stirred at 80°–90° C. for 2 hours. After cooling, it was diluted with 300 ml of water and the product extracted with ethyl acetate. The extract was dried over sodium sulfate, the solvent was evaporated and the oily residue purified by high pressure liquid chromatography (HPLC) (hexane:ethyl acetate=1:1). The desired fractions were combined, concentrated and recrystallized from isopropanol. The yield was 2.0 g, mp 219°–220° C.

Analysis: Calculated for $C_{11}H_9ClN_2O$: 59.86%C; 4.08%H; 12.70%N. Found: 59.61%C; 4.10%H; 12.48%N.

EXAMPLE 24

8-Chloro-1,2-dihydro-2-methyl-3H-1,4-oxazino[2,3-c]quinoline

A solution of 10 g of 3-bromo-7-chloro-N-(2-hydroxy-1-methylethyl)-4-quinolinamine in 28 ml of DMF was stirred and to it was added 4.3 g of potassium-t-butoxide. The mixture was stirred at 120°–140° C. for 2 hours and then allowed to cool to room temperature. The reaction mixture was diluted with water and the organics were extracted into dichloromethane. Washing with water, drying over anhydrous magnesium sulfate and evaporation of solvents resulted in a crude solid which was purified by HPLC using 2:1 hexane/ethyl acetate as the eluent. Recrystallization from acetone yielded 2.5 g of solid with a melting point of 215°–217° C.

Analysis: Calculated for $C_{12}H_{11}ClN_2O$: 61.41%C; 4.73%H; 11.94%N. Found: 61.14%C; 4.70%H; 11.72%N.

EXAMPLE 25

1,2-Dihydro-3-methyl-3H-1,4-oxazino[2,3-c]quinoline

Potassium tertiary butoxide (5 g) was added to a solution of 3-bromo-N-(2-hydroxypropyl)-4-quinolinamine (9 g) in 30 ml of DMF and the mixture stirred at 140° C. for 4 hours. The mixture was cooled to room temperature and poured into 200 ml of water. The product was extracted with dichloromethane and purified by HPLC (solvent: DCM:MeOH=10:1).

Analysis: Calculated for $C_{12}H_{12}N_2O_2$: 72.00%C; 6.00H; 14.00%N. Found: 71.99%C; 5.87%H; 14.10%N.

EXAMPLE 26

1,2-Dihydro-3,5-dimethyl-3H-1,4-oxazino[2,3-c]quinoline

A mixture of 18.5 g of 3-bromo-N-(2-hydroxypropyl)-2-methyl-4-quinolinamine and 7.0 g of potassium tert-butoxide in 100 ml of DMF was stirred at 80°–90° C. for 1 hour. The mixture was cooled to room temperature, diluted with 300 ml of ice-water and stirred for 1 hour, whereupon a solid separated which was filtered and recrystallized twice from isopropanol and finally from isopropyl acetate. The yield was 8.7 g, mp 169°–170° C.

Analysis: Calculated for $C_{13}H_{14}N_2O$: 72.87%C; 6.59%H; 13.08%N. Found: 72.94%C; 6.80%H; 13.03%N.

EXAMPLE 27

8-Chloro-1,2-dihydro-3-methyl-3H-1,4-oxazino[2,3-c]quinoline

A solution of 11 g of 3-bromo-7-chloro-N-(2-hydroxypropyl)-4-quinolinamine in 33 ml of dimethylformamide was stirred and to it was added 4.3 g of potassium t-butoxide. The mixture was stirred at 130°–140° C. for three hours and then allowed to cool to room temperature. The reaction mixture was diluted with water and the organics were extracted into dichloromethane. Washing with water, drying over anhydrous magnesium sulfate and evaporation of solvents resulted in a crude oil which was purified by HPLC using 2:1 hexane/ethyl acetate as the eluent. Recrystallization from acetone yielded 2.5 g of solid with a melting point of 239°–241° C.

Analysis: Calculated for $C_{12}H_{11}ClN_2O$: 61.41%C; 4.73%H; 11.94%N. Found: 61.09%C; 4.64%H; 11.87%N.

EXAMPLE 28

1,2-Dihydro-3-hydroxymethyl-3H-5-methyl-1,4-oxazino[2,3-c]quinoline

A mixture of 3-bromo-N-(2,3-dihydroxypropyl)-2-methyl-4-quinolinamine, potassium tert-butoxide (4 g) and DMF (50 ml) was stirred at 90° C. for 4 hours. Thereafter, it was diluted with 500 ml of water and saturated with potassium carbonate, and the resultant solid was filtered. The filtered liquid was extracted 5 times with dichloromethane. The dichloromethane-layer was dried over anhydrous magnesium sulfate and concentrated. The residue and the filtered solid were combined, purified by HPLC (DCM:MeOH=10.3) and recrystallized from isopropanol. The yield was 2.8 g, mp 197°–199° C.

Analysis: Calculated for $C_{13}H_{14}N_2O_2$: 67.81%C; 6.13%H; 12.17%N. Found: 67.72%C; 6.08%H; 12.02%N.

EXAMPLE 29

1,2-Dihydro-3-phenyl-3H-1,4-oxazino[2,3-c]quinoline

Sodium hydride (obtained from 2 g of 50% suspension in mineral oil) was added to a solution of 3-bromo-N-(2-hydroxy-2-phenylethyl)-4-quinolinamine (10 g) in 50 ml of DMF and the mixture was stirred at 90° C. for two hours. After cooling to room temperature, it was poured into 250 ml of water and the product extracted with two portions of 100 ml dichloromethane. The dichloromethane layer was dried over sodium sulfate and concentrated. The oily residue was dissolved in 80 ml of isopropanol, the solution was poured into 250 ml of ice water and the mixture was stirred for 1 hour. The solid was filtered and recrystallized from isopropanol. The yield was 3.1 g, mp 194°–195° C.

Analysis: Calculated for $C_{17}H_{14}N_2O$: 77.86%C; 5.34%H; 10.68%N. Found: 77.85%C; 5.30%H; 10.81%N.

EXAMPLE 30

Spiro[cyclohexane-1,3'-[3H][1,4]oxazino[2,3-c]quinoline]

A mixture of 5.5 g of 3-bromo-N-(1-hydroxycyclohexylmethyl)-4-quinolinamine, 2.2 g of potassium tert-butoxide and 50 ml of DMF was heated at 130° C. for 1 hour and then poured into 250 ml of water. The product was extracted with dichloromethane and ethyl acetate, dried and concentrated, and the residue was purified by HPLC using dichloromethane:MeOH=95:5 as the eluent. The fractions containing the product were combined and concentrated. The residue was taken up in water and stirred for 1 hour, and the solid was filtered and recrystallized from toluene. The yield was 2.6 g, mp 164°–165° C.

Analysis: Calculated for $C_{16}H_{18}N_2O$: 75.59%C; 7.09%H; 11.02%N.

Found: 75.44%C; 6.99%H; 10.95%N.

EXAMPLE 31

8'-Chloro-spiro[cyclohexane-1,3'-[3H][1,4]oxazino[2,3-c]quinoline]

A solution of 16.4 g of 3-bromo-7-chloro-N-[1-hydroxycyclohexylmethyl]-4-quinolinamine in 176 ml of dimethylformamide was stirred at room temperature and to it was added 7.54 g of potassium tert-butoxide. The mixture was heated at 130°–140° C. for twenty hours. The reaction mixture was then cooled to room temperature, quenched with water, and extracted with an ether/ethyl acetate solution. Evaporation of solvents resulted in a crude oil which was purified by HPLC using 2:1 hexane/ethyl acetate as the eluent. A solid resulted which was recrystallized from isopropanol to yield 4 g of crystalline solid with a melting point of 216°–218° C.

Analysis: Calculated for $C_{16}H_{17}ClN_2O$: 66.54%C; 5.94%H; 9.70%N. Found: 66.26%C; 5.89%H; 9.42%N.

EXAMPLE 32

1-(2-Cyanoethyl)-1,2-dihydro-3H-1,4-oxazino[2,3-c]quinoline

A solution of 2 g of 1,2-dihydro-3H-1,4-oxazino[2,3-c]quinoline, 1.15 g of acrylonitrile, 9.6 g of potassium hydroxide and 0.7 g of tetrabutylammonium bromide in 72 ml of toluene was stirred at room temperature for 16 hours. After this time there remained some starting material, therefore, it was necessary to add 50% more acrylonitrile to the reaction vessel. The mixture was stirred for 5 more hours and then washed with water (2×50 ml). Evaporation of solvents resulted in an oil which was purified by HPLC using 2:1 ethyl acetate/hexane as the eluent. Rcrystallization from isopropyl acetate gave 2.11 g of solid with a melting point of 104°–107° C.

Analysis: Calculated for $C_{14}H_{13}N_3O$: 70.28%C; 5.48%H; 17.56%N. Found: 69.99%C; 5.31%H; 17.29%N.

We claim:

1. A compound having the formula

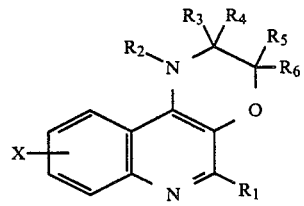

where X is hydrogen, loweralkyl, loweralkoxy, hydroxy, halogen, nitro or trifluoromethyl; $R_1$ is hydrogen or loweralkyl; $R_2$ is hydrogen, loweralkyl, arylloweralkyl or —$(CH_2)_mR_7$ wherein m is 1, 2 or 3 and $R_7$ is cyano or amino; $R_3$ and $R_4$ are independently hydrogen or loweralkyl; $R_5$ and $R_6$ are independently hydrogen or loweralkyl, or $R_5+R_6$ taken together with the carbon atom to which they are attached constitute a cyclobutane, cyclopentane, cyclohexane, cycloheptane, pyrrolidine, piperidine, morpholine or thiomorpholine ring, or $R_5$ is hydrogen and $R_6$ is aryl or —$CH_2OR_8$ wherein $R_8$ is hydrogen, loweralkyl or loweralkylcarbonyl, or a pharmaceutically acceptable acid addition salt thereof.

2. The compound as defined in claim 1, where $R_2$ is hydrogen.

3. The compound as defined in claim 1, where $R_1$ is hydrogen or methyl.

4. The compound as defined in claim 1, where X is hydrogen or halogen.

5. The compound as defined in claim 2, where $R_4$ is hydrogen or methyl and $R_3$, $R_5$ and $R_6$ are each hydrogen.

6. The compound as defined in claim 2, where $R_6$ is methyl, hydroxymethyl or phenyl and $R_3$, $R_4$ and $R_5$ are each hydrogen.

7. The compound as defined in claim 2, where $R_5$ and $R_6$ taken together with the carbon atoms to which they are attached constitute a cyclohexyl ring.

8. The compound as defined in claim 5, where X is hydrogen or halogen.

9. The compound as defined in claim 6, where X is hydrogen or halogen.

10. The compound as defined in claim 7, where X is hydroen or halogen.

11. The compound as defined in claim 8, which is 1,2-dihydro-3H-1,4-oxazino[2,3-c]quinoline.

12. The compound as defined in claim 8, which is 1,2-dihydro-5-methyl-3H-1,4-oxazino[2,3-c]quinoline.

13. The compound as defined in claim 8, which is 8-chloro-1,2-dihydro-3H-1,4-oxazino[2,3-c]quinoline.

14. The compound as defined in claim 8, which is 8-chloro-1,2-dihydro-2-methyl-3H-1,4-oxazino[2,3-c]quinoline.

15. The compound as defined in claim 9, which is 1,2-dihydro-3-methyl-3H-1,4-oxazino[2,3-c]quinoline.

16. The compound as defined in claim 9, which is 1,2-dihydro-3,5-dimethyl-3H-1,4-oxazino[2,3-c]quinoline.

17. The compound as defined in claim 9, which is 8-chloro-1,2-dihydro-3-methyl-3H-1,4-oxazino[2,3-c]quinoline.

18. The compound as defined in claim 9, which is 1,2-dihydro-3-hydroxymethyl-3H-5-methyl-1,4-oxazino[2,3-c]quinoline.

19. The compound as defined in claim 9, which is 1,2-dihydro-3-phenyl-3H-1,4-oxazino[2,3-c]quinoline.

20. The compound as defined in claim 10, which is spiro[cyclohexane-1,3'-[3H][1,4]oxazino[2,3-c]quinoline].

21. The compound as defined in claim 10, which is 8'-chlorospiro[cyclohexane-1,3'-[3H][1,4]oxazino[2,3-c]quinoline].

22. The compound as defined in claim 1 where $R_1$ is cyanoethyl.

23. The compound as defined in claim 22, which is 1-(2-cyanoethyl)-1,2-dihydro-3H-1,4-oxazino[2,3-c]quinoline.

24. A pharmaceutical composition comprising an effective memory enhancing amount of a compound as defined in claim 1 and a suitable carrier therefor.

25. A method of treating a patient in need of memory enhancement which comprises administration of an effective memory enhancing amount of a compound as defined in claim 1.

* * * * *